(12) United States Patent
Ferea et al.

(10) Patent No.: US 6,905,826 B2
(45) Date of Patent: Jun. 14, 2005

(54) METHODS AND COMPOSITIONS FOR MICROARRAY CONTROL

(75) Inventors: Tracy L. Ferea, Moutain View, CA (US); Gary P. Schroth, San Ramon, CA (US)

(73) Assignee: Applera Corporation, Foster City, CA (US)

( * ) Notice: Subject to any disclaimer, the term of this patent is extended or adjusted under 35 U.S.C. 154(b) by 85 days.

(21) Appl. No.: 10/050,188

(22) Filed: Jan. 14, 2002

(65) Prior Publication Data

US 2002/0110828 A1 Aug. 15, 2002

Related U.S. Application Data

(60) Provisional application No. 60/261,526, filed on Jan. 12, 2001.

(51) Int. Cl.[7] .......................... C12Q 1/68; C07H 19/00; C07H 21/00; C07H 21/02; C07H 21/04
(52) U.S. Cl. .................. 435/6; 435/91.2; 435/320.1; 536/22.1; 536/23.1; 536/23.4; 536/24.3; 536/26.6; 530/350
(58) Field of Search ..................... 536/22.1, 23.1, 536/24.3, 25.3, 26.6, 23.4; 435/6, 91.2, 320.1; 530/350; 935/77, 78

(56) References Cited

U.S. PATENT DOCUMENTS

| | | | |
|---|---|---|---|
| 5,563,034 A | 10/1996 | Brink et al. | |
| 6,001,983 A | 12/1999 | Benner | |
| 6,045,996 A | 4/2000 | Cronin et al. | |
| 6,228,575 B1 * | 5/2001 | Gingeras et al. | ................ 435/5 |
| 6,245,518 B1 | 6/2001 | Baier | |
| 6,309,824 B1 * | 10/2001 | Drmanac | ........................ 435/6 |
| 6,312,929 B1 * | 11/2001 | McMillan | .................. 435/91.1 |
| 6,362,004 B1 | 3/2002 | Noblett | |
| 6,423,535 B1 | 7/2002 | Arnold et al. | |
| 6,492,122 B2 | 12/2002 | Weidenhammer et al. | |

FOREIGN PATENT DOCUMENTS

| | | |
|---|---|---|
| EP | 0 810 230 A2 | 12/1997 |
| EP | 0 810 230 A3 | 4/1998 |
| WO | WO 00/06779 | 2/2000 |

OTHER PUBLICATIONS

International Search Report for PCT Application No. PCT/US02/00624, mailed Jan. 3, 2003.

* cited by examiner

*Primary Examiner*—Jezia Riley
(74) *Attorney, Agent, or Firm*—Finnegan, Henderson, Farabow, Garrett & Dunner, L.L.P.

(57) ABSTRACT

This invention relates to assay for detecting or determining the amount of target molecules in a sample. In certain embodiments, the invention relates to nucleic acid arrays and controls used in such arrays.

17 Claims, 5 Drawing Sheets

A competitive hybridization between experimental target and control target labeled with two different colors. Note in this approach features are not detectable unless a hybridization event occurs.

Close up view showing 342 features of a 55K (1X0.6 in) feature array of spotted dye.

A competitive hybridization between experimental target and control target labeled with two different colors. Note in this approach features are not detectable unless a hybridization event occurs.

Put a third signal into each feature during manufacturing of the array. Use third signal for spot finding and quantitation. A competitive hybridization between biologically derived experimental and control targets labeled with two different colors is then performed.

Deposit each feature without label. Perform non-competitive hybridization to array probes using a synthetic green-labeled control oligo and red-labeled cDNA samples. Requires a hybridization reagent containing a single green-labeled control oligo complementary to each feature on the array. Use green signal for spot finding and quantitation.

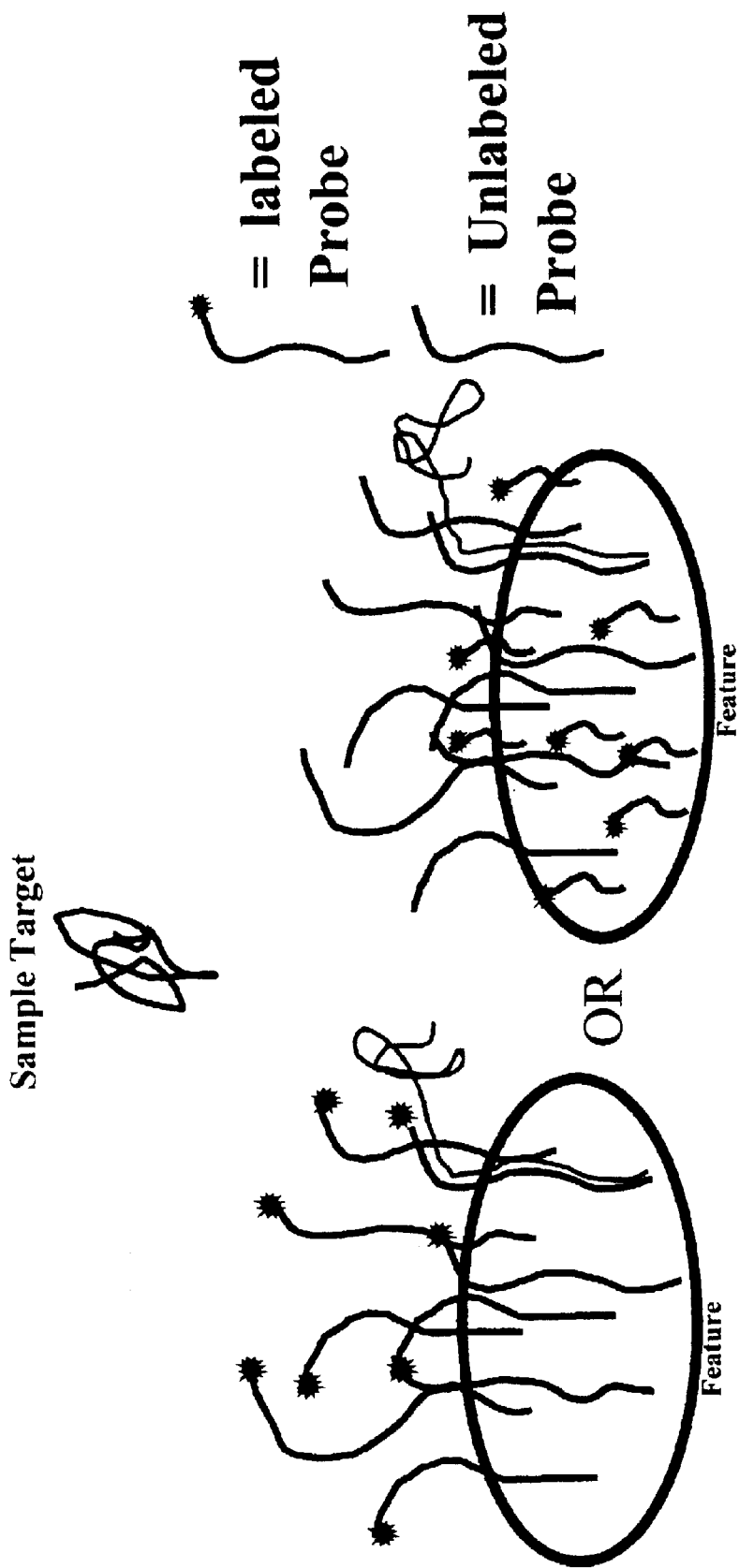

Figure 5
Put a label into each feature during manufacturing of the array. Label placed either directly on probe oligos or onto different co-spotted oligos. Use green dye for feature finding and quantitation. A gene expression assay would include a 1-color hybridization of red-labeled experimental target onto array. Use green signal to help better quantitate signal in red channel.

US 6,905,826 B2

METHODS AND COMPOSITIONS FOR MICROARRAY CONTROL

RELATED APPLICATION INFORMATION

This application claims the filing date benefit of U.S. Provisional Patent Application Ser. No. 60/261,526, filed Jan. 12, 2001, which is incorporated by reference in its entirety for any purpose.

DESCRIPTION OF THE INVENTION

Background of the Invention

This invention relates to assays for detecting or determining target molecules in a sample. In certain embodiments, it relates to nucleic acid arrays and controls used in such arrays.

Substrate-bound oligonucleotide arrays, also known as microarrays, enable one to test the hybridization of different nucleic acid sequences in a sample to many different oligonucleotide probes. These arrays can be composed of hundreds of thousands of probes deposited or synthesized within specific regions, defined as features, on a substrate such as a glass microscope slide or other materials. (See, e.g., FIG. 1.) In some procedures, one may use target nucleic acid directly from a sample (as mRNA, for example). In some procedures, one may use target nucleic acid replicated or amplified from a sample (as cDNA, for example). Hybridization assays on such arrays may be used for profiling of gene expression levels, identification of genetic variants of infectious diseases, identification of genetic diseases, or any assay that identifies different nucleic acid sequences.

Target nucleic acid is typically labeled with a detectable marker, such as a fluorescent molecule. Hybridization between a target and a probe is detected by a fluorescent signal at various features within the array. The amount of signal can be dependent on the amount of target available for hybridization, as well as the thermal stability of the probe-target hybrids. Thermal stability is a function of several factors. For example, the length of the hybridizing region, the accuracy of the match in hybridization, the total length of the oligonucleotides, as well as the actual sequence composition (A–T rich regions melt at lower temperatures than G–C rich areas), all factor into the specific melting point (Tm) for a probe-target hybrid.

Currently, quantitation of a signal is often performed by comparing the signal from an experimental target sample with an arbitrary biological reference (or "control") sample that competitively hybridizes to the same feature. (See, e.g., FIG. 2.) Thus, comparisons are made within the same feature. For many biologically derived samples, it is often difficult to either obtain or determine the proper control for an experiment. Biologically derived controls also have problems with reproducibility. Also, such controls typically do not include a target sequence corresponding to every different probe sequence for each feature on an array. Thus, some features may never have control target sequences that can provide a signal.

With current methods, an absence of any control signal for any given feature may be caused by a lack of a sufficient amount of that specific target in the control, or by a lack of sufficient probe bound to the feature. These two causes, which have profoundly different biological implications, typically cannot be distinguished.

The shape of each feature can also affect the apparent amount of signal read at a given locus. A smaller feature creates a smaller area lit by the signal, and consequently an imaging system may read less signal. Also, it is often important to differentiate between background and actual signal at any given feature.

Thus it is important to determine pixels at a given feature that are properly attributed to a positive signal rather than to background.

It can be difficult to quantitate accurately the number of probe molecules attached to a feature. This makes it difficult to accurately quantitate signal obtained from hybridization. Consequently, it is difficult, if not impossible, to compare signals obtained from hybridization to different probes at different features within an array, as well as to compare signals obtained from the same probe on the same array or signals obtained from the same probe on different arrays.

SUMMARY OF THE INVENTION

In certain embodiments of the invention, synthetic control elements are provided. In certain embodiments, the controls comprise nucleic acid sequence control probes that are included in each feature. In certain embodiments, such bound control probes hybridize to labeled control target sequences, but do not hybridize to target sequences in the experimental sample. In certain embodiments, the control probe sequence may be attached to or contiguous with an experimental probe. In certain embodiments, the control probe may be bound to the substrate separate from the experimental probe.

In certain embodiments, a control label is included in each feature of the array, which provides a control signal that indicates the amount of probe attached. In certain embodiments, a control label may be attached directly to at least some of the probes of each feature. In certain embodiments, the control label is provided by a nucleic acid molecule with a label attached, and the nucleic acid molecule is designed such that it does not hybridize to nucleic acids in an experimental sample.

In certain embodiments, the label that is attached to the feature may provide any number of signals, in addition to the signals provided by an experimental target signal and a control target signal.

In certain embodiments, labeled control sequences are provided such that there is a synthetic control sequence corresponding to all of the probes on all of the features.

In any of these embodiments, the experimental probes on any given feature may have the same sequence for hybridization to a specific target sequence in the sample. Also, in any of these embodiments, any given feature may contain more than one different experimental probe sequence for hybridization to different target sequences in the sample.

Kits for quantitating the signal and the attached probe are also provided. In certain embodiments, these kits comprise an array that has been created using the inventive methods. Kits further comprising an array and a synthetic control target are also provided.

BRIEF DESCRIPTION OF THE FIGURES

FIG. 5 shows hybridization using labeled probes.

DETAILED DESCRIPTION OF THE INVENTION

Figure 1:
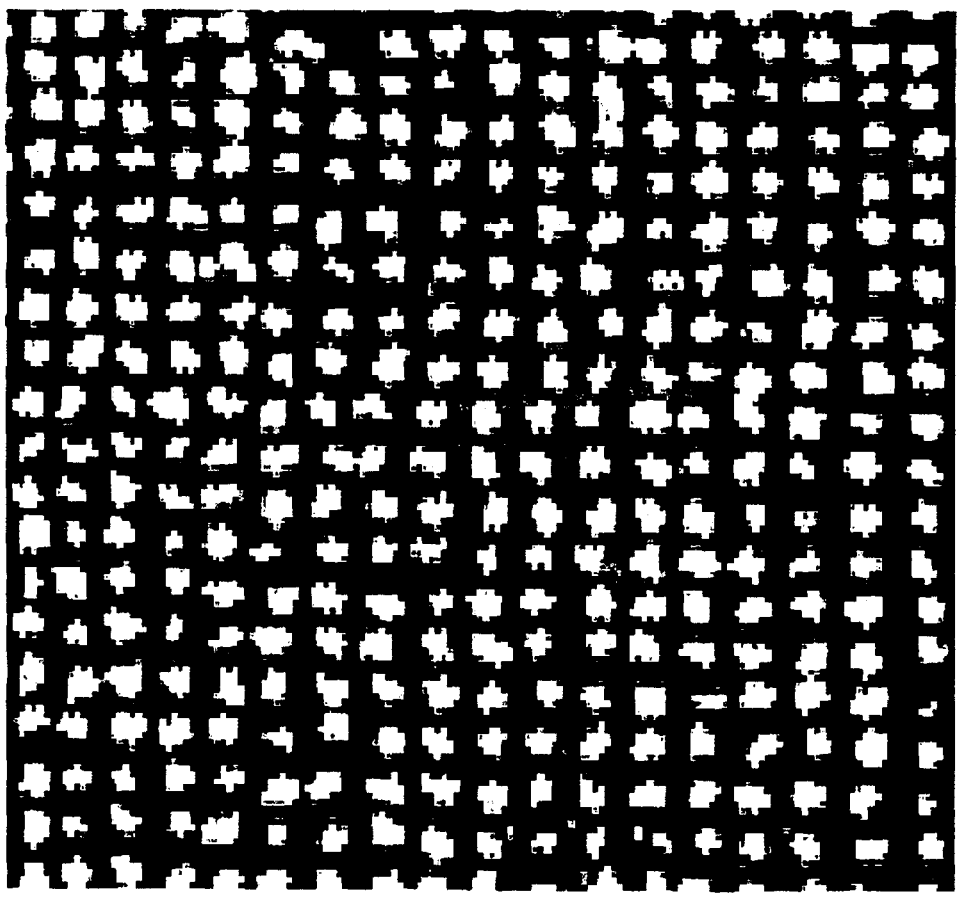
FIG. 1 shows a close-up view of 342 features of a 55K (1 in×0.6 in) array with a fluorescent label.
Figure 2:
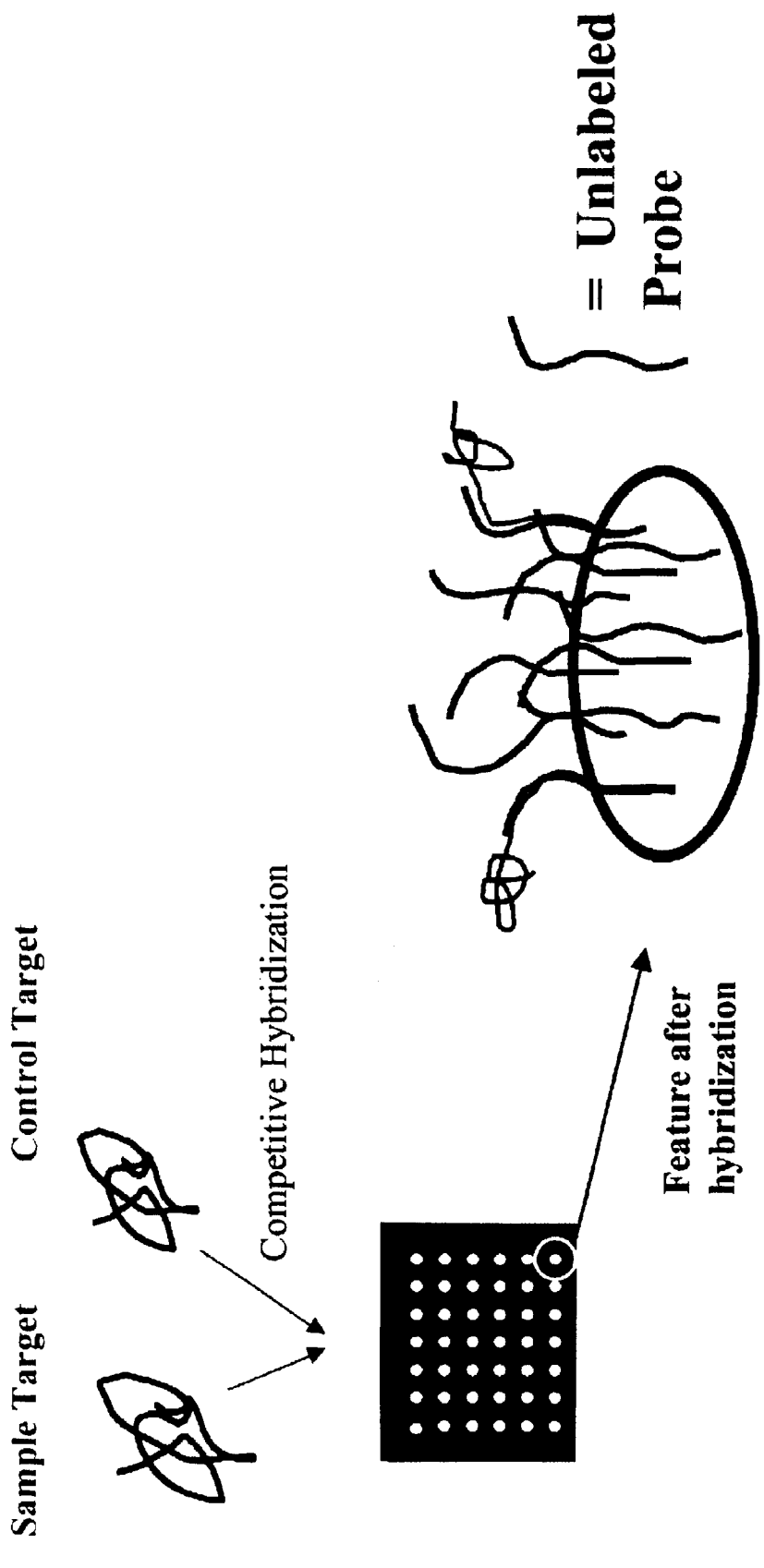
FIG. 2 shows competitive hybridization between experimental target and control target labeled with two different colors.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose.

Definitions

The term "complement" refers to the compatibility of two sequences and their ability to match and form a hybrid. Thus, a target can be said to be a complement of the probe.

A "probe" is an oligonucleotide that is attached to the substrate of the array, and that is capable of binding to a complementary target sequence. The probe may include Watson-Crick bases or modified bases. Modified bases include, but are not limited to, the AEGIS bases (from Eragen Biosciences), which have been described, e.g., in U.S. Pat. Nos. 5,432,272; 5,965,364; and 6,001,983. Additionally, bases may be joined by a natural phosphodiester bond or a different chemical linkage. Different chemical linkages include, but are not limited to, a peptide bond or a Locked Nucleic Acid (LNA) linkage, which is described, e.g., in published PCT applications WO 00/56748; and WO 00/66604.

In certain embodiments, control probes bind to control target sequences, and experimental probes bind to experimental target sequences. In certain embodiments, the control probes and experimental probes are contiguous (e.g., they may be made as one oligonucleotide or they may be attached to one another in any suitable manner).

"Target" nucleic acids are those nucleic acids capable of hybridizing to probes.

An "experimental target sample" is one or more nucleic acid molecules from a test sample that are used in an assay. The experimental target sequences are those that may be identified or quantified after they hybridize to experimental probes on the array. In certain embodiments, the experimental target sample may be extracted directly from the sample, e.g., as RNA or DNA. In certain embodiments, the sample may be replicated from the sample nucleic acid, e.g., such as cDNA which has been reverse transcribed from sample mRNA. Finally, the experimental target sample may also be amplified from the sample nucleic acid.

A "control target" is a nucleic acid that can hybridize to probes to give a reference signal. In certain embodiments, such control targets can be used as a reference against which the signal from the experimental target may be compared. The control target may compete, or may be non-competitive with, the experimental target. Thus, a single control target molecule may or may not compete with an experimental target molecule for binding to a single probe molecule.

The term "feature" refers to a single location deposited on an array which is read as a single data point. In certain embodiments, a single feature may have probes that all have the same sequence. In certain embodiments, a single feature may include probes with different sequences.

The arrays in certain embodiments of the invention can be used for any identification or separation of nucleic acid sequences. Examples include, but are not limited to, nucleic acid expression analysis, identification of tagged molecules in a sample, and separation of tagged molecules out of a sample.

Reliable Controls

Certain embodiments of the present inventions are directed to methods, compositions, and kits which provide quality control for the manufacture of the arrays. In certain embodiments, the invention can provide quantitation of signal to facilitate comparison between features within an array, comparison with features on other arrays, and comparison of multiple features on multiple arrays. Such embodiments provide reliable and consistent control signals against which the experimental signal can be compared.

The manufacture of high density nucleic acid arrays, and methods of their use in diagnostic assays have been described in U.S. Pat. Nos. 5,445,934; 5,552,270; 5,837,832; 6,040,138; and 6,045,996; and published PCT applications WO 00/39345 and WO 00/47767.

During manufacture, errors may occur during the depositing of probes on features within the array. Thus, there may be no probe deposited at a particular feature, or there may be variation in the amount of probe deposited at different features within an array or variation at counterpart features in different arrays. Such variation in probe deposition (including failure of probe attachment) may occur due to many factors. For example, the reactivity of the surfaces may vary from feature to feature and/or from array to array, different elements that are used for depositing probe at different features or on different arrays may create variation in the amount and distribution of probe, and differing environmental conditions, such as humidity, can impact probe deposition. Since the attachment typically involves a chemical binding reaction with the probe or with linkers, variations in such reactions, or the if absence of active reagents, can create variations in probe deposition. Variation may result during any method for attaching nucleic acid on a substrate, e.g., during in situ synthesis of probe on a substrate. Variation may often result when arrays are made in different facilities, but also may result within the same facility.

An aim of certain embodiments of the invention is to account for such variation and to provide more accurate determination of amounts of sequences within an experimental sample. Thus, according to certain embodiments, the present invention allows one to determine whether sufficient probe is actually attached to an individual feature. In such embodiments, if no signal is detected for a given feature, the user can typically conclude that insufficient probe was bound to the substrate. Without such appropriate controls, when one uses the array, such a lack of signal may indicate that there was not sufficient complementary control target or experimental target in the sample, but it could also indicate that there was insufficient probe attached to the feature. The user would not be able to make a conclusion one way or the other. Thus, such embodiments of the present invention provide an important control for the user.

Also, certain embodiments provide appropriate controls for manufacturing arrays. In certain embodiments, one can determine whether probe has attached to each feature without running a hybridization reaction. In certain embodiments, the controls can be used in hybridization reactions to test batches of arrays to provide quality control for appropriate probe deposition.

Also, according to certain embodiments, the invention provides more consistent controls for comparing experimental signals, which allows one to obtain an accurate ratio of experimental signal to control signal. That ratio allows one to more accurately compare that feature to other features on that array, or to features on other arrays when one employs the same controls on such other arrays.

Also, with different features on an array or on features of different arrays, variation in intensity of signal may be due to variation in the amount of experimental target in a sample, or may be due to variation in the amount of probe in counterpart features. In certain embodiments, the present invention allows one to determine whether such variation is due to variation in the amount of probe, since the control signal is not dependant on the amount of experimental or control target in the sample. Such embodiments include more consistent controls, which allows one to obtain a more accurate ratio of experimental signal to control signal. That ratio allows one to more accurately compare that feature to other features on that array, or to features on other arrays when one employs the same controls on such other arrays.

Also, when microarrays are placed in an optical reader, small misalignments, e.g., caused by misplacement of the array in the reader or by misalignment during array manufacture, may result in errors in identifying the source of a signal. In some known arrays, some features in the array are used to spot a label without probe in order to serve as a "landmark" in aligning the array. This results in fewer features available for experiments, and does not provide controls for the amount of probe deposited on the other features.

According to certain embodiments of the invention, a "landmark" is provided in features along with experimental probe. According to certain embodiments, deposition of control label in easily identifiable patterns allows the features to provide a "landmark" function for aligning the array without sacrificing the number of features used for the assay. The landmark function also allows for easier identification of specific features within the array.

In some methods of array manufacture, features are deposited in an array on a polymeric substrate. According to certain embodiments, one can use polymeric film and methods of affixing nucleic acids such as those disclosed in published PCT application WO 99/53319. After attachment of the probes, the polymeric film is heated. In certain embodiments, it shrinks about twenty-five fold, to about four percent of its original size. After shrinking, the plastic substrate typically has folds on the surface approximately 10 microns across. The features typically are approximately 40 microns across. Such folding can create an irregular and uneven focal plane, and an indefinite depth of field.

Having a control signal at each feature typically allows one to correct for irregularities in the shape, size, and intensity of the feature, as well as in the focal plane and the depth of field. According to certain embodiments, placing the array on a larger surface which is shrunk allows for finer detail in depositing desired shapes for the feature, and greater regularity in probe density. Because one is initially depositing a larger feature that is later reduced in size, feature landmarks typically become easier to shape to provide useful landmarks for aligning arrays.

Also, according to certain embodiments, features are outlined with control signal. This allows one to scan features that are defined by the control signal, and disregard areas with no control signal. Areas without control signal would have no attached experimental probe. Thus, one can determine what part of the feature is background and that background should not be included in the quantitation of the features. This would make the reading of any experimental signal accurate.

In certain embodiments the identifiable pattern formed is a pattern of pixels, such as those read by an optical scanner. Detection of a control signal within a pixel indicates that probe is present within that pixel. Those pixels with no control signal are then known to be background. One can then easily distinguish the pixels which are part of the feature from the background, and scan for experimental signal only in those pixels which are part of the feature.

Certain embodiments of the invention are directed to software that is used for analysis of the controls. For example, software can be used for quantitation and comparison of the various signals from different features and/or from different arrays.

Examples of Controls

In the following, methods of providing a control system for certain embodiments are described. In all of the embodiments, the control signal can be used to confirm that experimental probe is present in a feature and can be used to help quantitate the experimental signal. In all the embodiments in which a control signal is present at a feature, that control signal can also be used to define the shape of the feature. In such embodiments where a control signal is present in a feature, the outline of the feature may be used to positively identify where experimental probe is bound, and distinguish that area from background where no experimental probe is bound.

In any of the embodiments of this invention, the probes and the labeled molecules can be attached to the substrate in any manner. In certain embodiments, the probes and labeled molecules are attached covalently to the substrate. In certain embodiments, the probes and labeled molecules are attached by other methods, including but not limited to UV cross-linking, electrostatic attachment, polylysine coating of the substrate, hybridization to other nucleic acids on the substrate, and in situ synthesis of the nucleic acid on the substrate. In certain embodiments, the probes and labeled molecules are attached with a linker molecule. Certain embodiments include, but are not limited to, polyethylene glycol linker molecules, peptide linker molecules, or C6 linker molecules.

In certain embodiments, the control label is attached to the feature along with the probe. The label may be conjugated onto the experimental probe, or onto a different molecule. In certain of these embodiments, when the label is attached to a different molecule, the labeled molecule can be attached to the feature using the same chemical reaction or linker that is used to attach the probes. In certain embodiments, label is conjugated to a subset of the experimental probes, such that a specific percent of the probe molecules bound to the feature are labeled. One can control the ratios of the unlabeled probe and the labeled probe in the sample, thus the signal from the labeled probe can be used to calculate the amount of total experimental probe bound to a feature.

In certain embodiments, one may want to have a control for determining whether hybridization occurs. In certain embodiments, a feature is deposited on an array with a control probe that hybridizes to a control target known to be in the sample. Detection of the complementary control target oligonucleotide at the control probe feature indicates that hybridization is occurring.

In certain embodiments, each feature of the array contains a nucleic acid control probe which is not complementary to any experimental target sequence. In such embodiments, one uses a control target that is complementary to the control probe. The control target does not compete for binding with the experimental target. In certain embodiments, one uses control probes that all have the same nucleic acid sequence and control targets that all have the same sequence that is complementary to the control probe sequence. Thus, in these embodiments, a different control sequence need not be included for each different array feature. This reduces the number of synthesis reactions used to make the control targets for the assay.

To decrease the chance of cross hybridization with experimental targets, in certain embodiments, the control probes and control targets may include non-Watson-Crick bases. Such bases typically would not be included in experimental targets from a biological sample, and typically would not hybridize with the naturally occurring Watson-Crick bases in the experimental probes and experimental targets. Synthetic non-Watson-Crick bases, such as the AEGIS bases, are described, e.g., in U.S. Pat. Nos. 5,432,272; 5,965,364; and 6,001,983, available from Eragen Biosciences, Inc.

In certain embodiments, the non-competitive control probe is attached to the experimental probe (e.g., the control probe and target probe can be synthesized as one oligonucleotide). The two contiguous probes are then attached to the substrate. The attachment to the substrate may occur through the control probe, the experimental probe, or a linker that is attached to one of the probes. This method has an added advantage that the stochiometry of experimental and control probes within a feature is the same. Thus, in these embodiments, by determining signal from the control target that binds to the control probe one can easily determine not only whether experimental probe has bound to the substrate, but also the amount of such binding.

In other embodiments, the non-competitive control probe is not contiguous with the experimental probe, and is bound to the substrate with the same substrate binding reaction as the experimental probe. These embodiments provide a control for determining the amount of experimental probe that is attached to the feature. Because the control and experimental probes bind to the substrate by the same chemical reaction, the amount of control probe that is detected in a feature should be representative of the amount of experimental probe that is also attached to that feature. Thus, failure to attach experimental probe or variations in the amount of experimental probe bound to the substrate can be detected by observing the amount of control signal obtained after hybridization of the control target to the control probe.

In certain of these embodiments, one prepares a predetermined ratio of control probe to experimental probe. Thus, a reliable and consistent control signal can be added to the array quickly.

Figure 3:
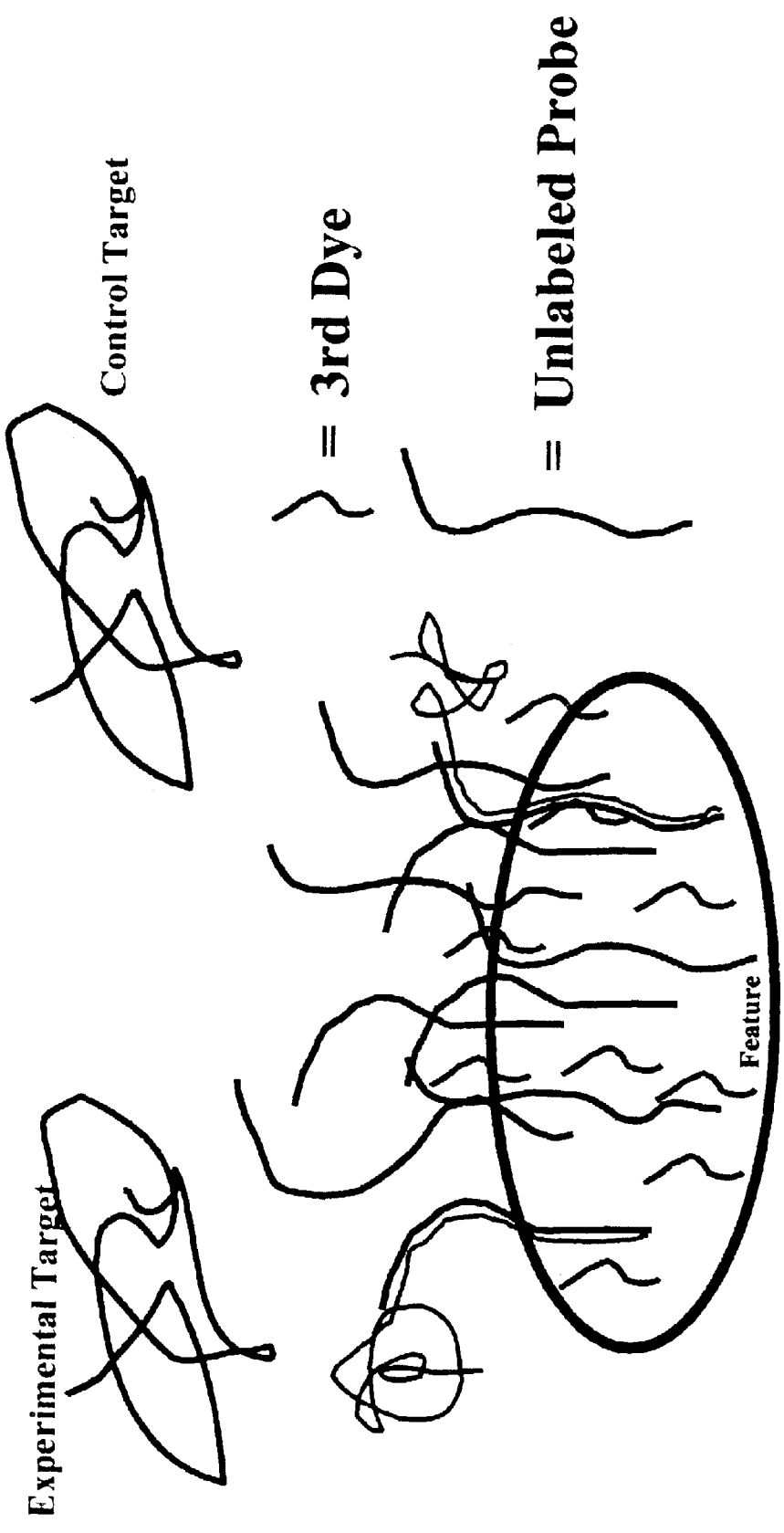
FIG. 3 shows a third signal approach, where a third label is attached to each feature during manufacture of the array. The third signal can provide for feature identification and quantitation. A competitive hybridization between experimental and control targets using two other signals may be performed with such embodiments. Also, the competitive hybridization may be performed with two experimental targets from two different samples using two other signals.

In certain embodiments, one employs labeled experimental targets (a first signal), labeled control targets (second signal), and control labels that are attached to the features during array manufacture (a third signal). (See FIG. 3.) In these embodiments, the third signal provides a control for accurately determining the amount and placement of experimental probe that is bound to the feature. The amount of a given control target in traditional biological derived control samples is typically not known. Thus, it is possible that a given control target sequence is not present in the control sample. Thus, without the third signal, absence of control signal at a feature cannot be positively attributed to lack of control target sequence in the sample or to the lack of experimental probe on the feature. Also, since the amount of control target typically is not known, one typically cannot accurately determine that differences in signal intensity from feature to feature is due to different levels of target in the sample or is due to different levels of probe bound to the substrate.

In these embodiments, the competitive hybridization is carried out with the experimental target (which provides a first signal if there is binding) and control target (which provides a second signal if there is binding). If one observes second signal at a feature, the control target signal can affirm that hybridization can occur with a given probe.

In certain embodiments, one can use three signals but replace the control target (with the second label) with a different experimental target that has the second label. Thus, within a single feature, one can determine whether there is complementary experimental target in two different samples. In certain embodiments, one could obviously increase the number of different experimental target samples with different labels. In certain embodiments, one could employ more than one experimental target sample along with the control target and the control attached to the feature. In such embodiments, one could use different labels for each experimental target sample as well as for the control target and the control attached to the feature.

In some instances, more than one experimental probe sequence may be employed for determining the amount of a target in a sample. For example, this may be useful in instances in which variations in splicing result in different mRNA transcripts for the same gene, which transcripts have different overall sequences. In such cases, it may be desirable to have different experimental probe sequences complementary to different portions of the gene located on the same feature. In certain embodiments of the invention, several experimental probes are created that are complementary to different regions of a transcript. These different experimental probes are deposited on the same feature. This would allow experimental target molecules representing a given gene a greater opportunity to hybridize to the feature. Any number of different experimental probes may be included in the same feature. Consequently, the experimental signal could be a more accurate indication of the levels of expression of a given gene in the sample, and only one feature is used to accomplish this result rather than multiple features. Of course these multiple experimental probes can be directed to other nucleic acids, such as intergenic regions, introns, etc.

Synthetic Control Targets

Reliable and consistent controls may also be provided by creating synthetic control targets. Such targets typically would not require any special array design, and could be used with arrays from different sources or from different manufacturers.

Under current methods, control targets are typically derived from biological samples. In an attempt to obtain a control target molecule which hybridizes to each feature, researchers have used pools of nucleic acid from several different tissues, or several different samples. This typically does not give reliable or consistent results.

According to certain embodiments of the invention, a synthetic control target sample or pool can be produced that includes known target sequences complementary to any number of features of an array. The amounts of such target sequences in such synthetic control target samples can also be known. Such pools of oligonucleotide targets provide a consistent control signal for the entire array and for different arrays.

According to certain embodiments, the synthetic control target sample can be used to quantify the amount of probe in the features by comparing the signal generated from the control targets to the signal generated from the experimental targets. In such embodiments, since one knows that there is control target that will hybridize to each probe that is supposed to be included on the array, one will always obtain control target signal if sufficient probe is attached to the feature. Thus, a lack of such control target signal indicates that insufficient probe is attached to the feature. Also, since one knows the quantity of control target, one can accurately quantify the amount of experimental target in a sample.

In certain embodiments of the invention, premade sets of synthetic control targets can be made to correspond to different sample types. For example, synthetic control targets can be compiled for known expressed transcripts from whole blood. This set of control targets could be used for any array designed to be used with experimental samples from whole blood. Similarly, synthetic control targets could be composed to correspond to an entire genome. Such a control target pool could be applicable to any diagnostic array designed for human samples.

In certain embodiments, the control targets are made from a set of oligonucleotides which contain a number of random nucleotide bases. In certain embodiments, the control targets are from about 6 to 30 bases, 8 to 15 bases, 10 to 12, or 10 bases in length. By using a number of random nucleotides, one increases the statistical likelihood that there would be some control target molecule which would bind to any given probe. This statistical likelihood may also be increased by using fewer than the typical 25 to 50 base length target oligonucleotides along with the random nucleotides. One may also accomplish an increased likelihood that control target molecule will bind to any given probe by increasing the concentration of the control target molecules. In these embodiments, the pool of control target oligonucleotides may be designed without knowing the particular probe sequences.

With shorter oligonucleotides, the melting temperature (Tm) is lower, which causes such short oligonucleotides to bind to their complements less efficiently. This possible problem typically can be solved by altering the chemical bonds between the bases. Nucleotide bases joined by peptide bonds, instead of the natural phosphodiester bonds, have higher melting temperatures. In certain embodiments, the control target is composed of short oligonucleotides of nine or ten bases in length, joined by peptide bonds or LNA linkages, such as those described in published PCT applications WO 00/56748; and WO 00/66604. Such targets have the Tm of much longer oligonucleotides, allowing them to withstand the stringent conditions typically used for hybridization assays.

EXAMPLES

The following prophetic examples are offered to more fully illustrate the invention, but do not limit the scope thereof.

Example 1

In this example, a standard nucleic acid array is created with a predetermined ratio of labeled control probe to unlabeled experimental probe. (See FIG. 5.) The total amount of probe bound to each feature is determined by examining the signals from the labels on the control probes, and calculating the total amount of probe based on the predetermined ratio. One can use this information to more confidently determine the relative amount of experimental target in a sample. Specifically, knowing the relative amount of experimental probe at two different features, one can more confidently determine whether variations in experimental signal intensity at different features is resulting from an actual difference of the level of experimental targets in the sample or is resulting from variations in the amount of experimental probe deposited at different features. This comparison may be accomplished by dividing the experimental signal by the control signal at each feature.

For example, assume that the experimental signal at a feature corresponding to Gene A in a first array is measured at 1000 arbitrary units. Also, assume that the control signal at the same feature is 250 units. This provides a ratio of 4:1 of experimental over control signal. Next, for a different experimental sample, assume that the signal at a feature for Gene A for a different experimental sample in a second array is measured at 400 units, and that the control signal at that feature on the second array is measured at 100 units. This also provides the same 4:1 ratio. Although the experimental signal at the Gene A feature on the second array is markedly less than the signal on the first array, the correction for the control signal indicates that the transcript in both samples appears to be expressed at the same level. This method may also be used to compare two different target sequences at different features in the same array.

Example 2

Figure 4:
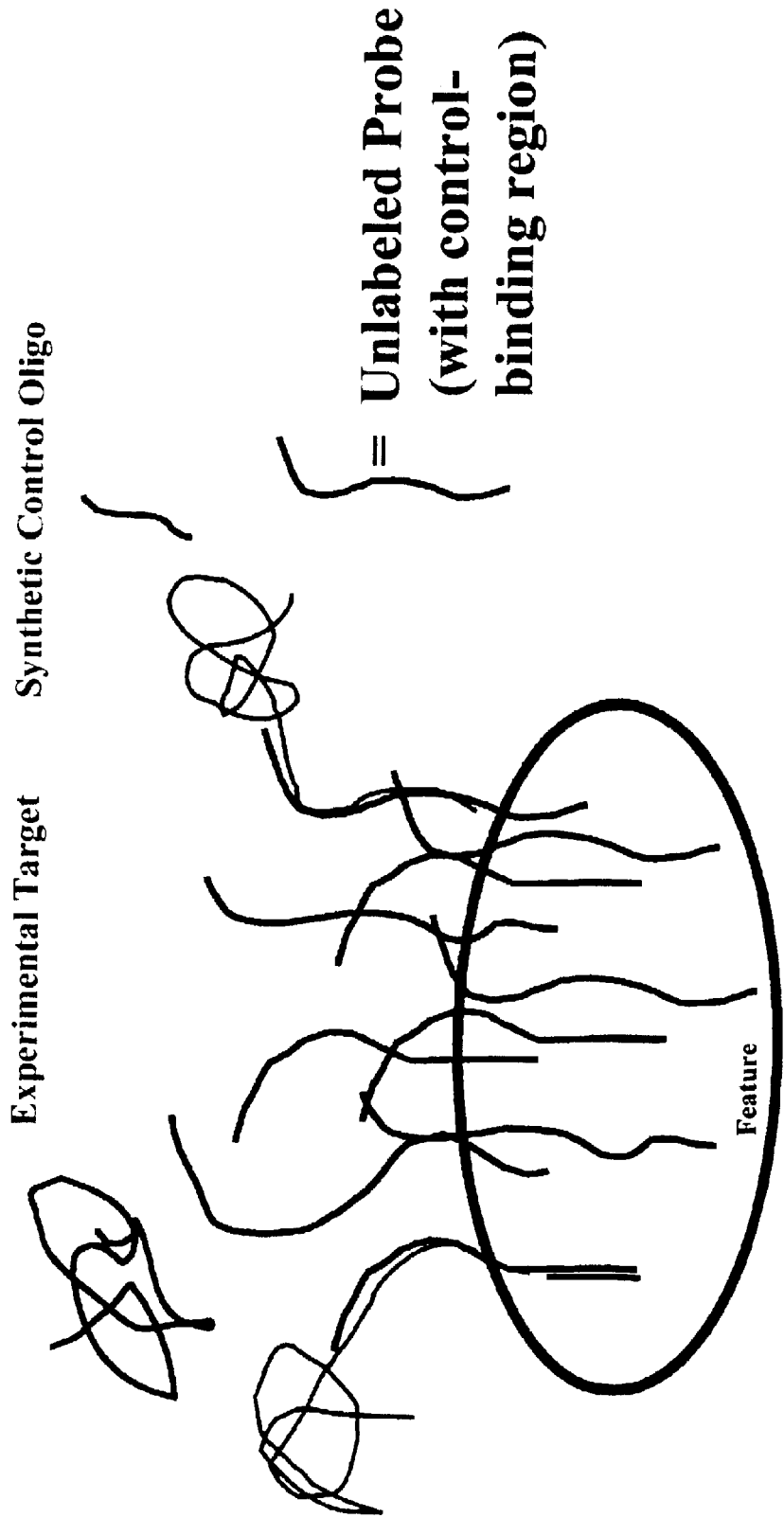
FIG. 4 shows a non-competitive hybridization using synthetic control targets that are complementary to a control probe. In this embodiment, the control probe is attached to the experimental probe.

In this example, at least some of the experimental probes for each feature include an attached or contiguous control oligonucleotide probe. (See FIG. 4.) The control probe is designed to minimize cross-hybridization with any of the intended experimental target molecules. The control oligonucleotide sequence can be identical in each feature.

During hybridization, one uses a control target, which complements the control probe oligonucleotide sequence. The control target hybridizes to the control probe. The control target does not compete with the experimental target hybridization, and thus does not interfere with the experimental target binding to the experimental probe portion of the same molecule. Because the control target has an identical number of molecules to bind to as the experimental target, the signal ratio is very accurate among all the features on the array. Also, because the control probe oligonucleotide sequence is identical in every feature, one can employ control targets all having the same sequence. Consequently, one can manufacture control targets with only one synthesis reaction.

Example 3

In this example, an array and a set of corresponding control targets are combined together as a kit. An array is designed as a specific diagnostic assay to search for a certain set of diseases in a human patient, such as a set of diseases known to affect various transcription levels in blood cells. A set of control target oligonucleotides is synthesized to correspond to each feature in the array. The features include different experimental probes that allow one to determine the amount of each transcript in the sample.

Example 4

A set of synthetic control target oligonucleotides are provided. The oligonucleotides represent every known transcript expressed in the liver. Included in the pool of control target oligonucleotides are those transcripts known to be expressed in liver in diseased or cancerous states. The entire pool of oligonucleotides is packaged as a synthetic liver control target kit. This synthetic control target kit can be employed in any nucleic acid array used as an assay on liver tissue, regardless of manufacturer, or the identity of the transcripts that are sought.

Example 5

This example refers to synthetic control targets which can be used on any array. In certain embodiments, control target oligonucleotides are generated using random bases in a number of places. Because the control target oligonucleotides are short in this embodiment (8 to 12 bases in length), and because they include several random bases, the probability that any probe would be complementary to at least one of the control target molecules is very high. Consequently, a pool of control target oligonucleotides is generated which is complementary to any probe on any array.

Because the control target oligonucleotides are short, they possess a low Tm (which varies based on their sequence composition). While a ten base-pair hybrid typically would not survive the stringent conditions necessary for a standard microarray hybridization assay, the oligonucleotides can be chemically modified to increase the Tm of their hybrids. For example, locked nucleic acids (LNA's) have inverted stereochemistries at C-3' and C-4' to provide an L-ribo confirmation. Bases joined by LNA's hybridize to their complements with high affinity, and have much higher melting temperatures than their naturally occurring counterparts with phosphodiester bonds.

The short control target oligonucleotides include a label attached. These synthetic control targets comprise a universal control target sample which provides a reliable and consistent control signal for the amount of probe sequence bound to each feature of the array, and provides a control signal that can be compared with the experimental signal for analysis. This synthetic control target sample can be used in any microarray assay, regardless of probe sequences or array manufacture.

While the present invention has been described in terms of these exemplary embodiments, the skilled artisan will readily understand that numerous variations and modifications of these embodiments are possible without undue experimentation. All such variations and modifications are within the intended scope of the claimed invention.

What is claimed is:

1. A method for detecting the presence or absence or amount of an experimental target-specific probe on a substrate comprising:

exposing a substrate containing a first feature comprising an experimental target-specific probe and a control-specific probe to a labeled control target, such that the labeled control target binds specifically to control-specific probe bound to the substrate, wherein the control-specific probe is not bound to the substrate by hybridization, and measuring a signal from labeled control target bound to control-specific probe to determine the presence or absence or amount of experimental target-specific probe;

wherein the substrate contains two or more features; and wherein at least one of the features does not comprise a control-specific probe.

2. The method of claim 1, wherein the experimental target-specific probe and control-specific probe are polynucleotides.

3. The method of claim 2, wherein the control-specific probes that are polynucleotides contain synthetic non-Watson-Crick bases.

4. The method of claim 1, wherein the control-specific probe is attached to the experimental target-specific probe.

5. The method of claim 1, wherein the control-specific probe is not attached to the experimental target-specific probe.

6. The method of claim 1, wherein the labeled control target comprises a fluorophore.

7. The method of claim 1, wherein the substrate is exposed to a labeled experimental target molecule in a sample, such that labeled experimental target molecule is bound to experimental target-specific probe.

8. The method of claim 7, wherein the signal from labeled control target bound to control-specific probe is used to quantitate the amount of labeled experimental target molecule in a sample.

9. The method of claim 1, wherein the substrate further contains a second feature comprising a second experimental target-specific probe and the control specific probe.

10. A method for detecting the presence or absence or amount of an experimental target probe on a substrate comprising:

exposing a substrate containing a feature comprising an experimental target probe to a labeled control target and a labeled experimental target, such that the labeled control target binds to experimental target probe bound to the substrate, wherein the experimental target probe is not bound to the substrate by hybridization, wherein the labeled control target competes with the labeled experimental target for binding to the experimental target probe, and measuring a signal from labeled control target bound to experimental target probe to determine the presence or absence or amount of experimental target probe.

11. A method for determining the relative amount of two different experimental target nucleic acid sequences in a sample, comprising:

providing a nucleic acid array, wherein the array comprises a first feature that comprises first experimental target-specific probes that are complementary to a first experimental target sequence and control-specific probes that do not hybridize to experimental target sequences, and a second feature that comprises second experimental target-specific probes that are complementary to a second experimental target sequence and control-specific probes that do not hybridize to experimental target sequences;

contacting the array with:
(1) a sample that includes experimental target sequences that are labeled with a first label; and
(2) synthetic control target sequences that are labeled with a second label and that hybridize to the control-specific probes on each of the first and second features, but that do not hybridize with the experimental target-specific probes;

determining the intensity of any signal from the first and second labels in the first and second features;

determining the ratio of the intensity of the signal from the first label to the intensity of the signal from the second label for each of the first and second features; and comparing the ratios of the intensity of the signal for the first and second features to calculate the relative amount of first and second experimental nucleic acid target sequences in the sample;

wherein the array comprises three or more features, and wherein at least one of the features does not comprise a control-specific probe.

12. A method for detecting the presence or absence or amount of an experimental target-specific probe on a substrate comprising:

exposing a substrate containing a first feature comprising an experimental target-specific probe and a control-specific probe to a labeled control target and a labeled experimental target, such that the labeled control target binds specifically to control-specific probe bound to the substrate, wherein the control-specific probe is not bound to the substrate by hybridization;

wherein the labeled control target comprises a first label and the labeled experimental target comprises a second label;

wherein the first label is distinguishable from the second label; and measuring a signal from labeled control target bound to control-specific probe to determine the presence or absence or amount of experimental target-specific probe;

wherein the substrate contains two or more features; and wherein at least one of the features does not comprise a control-specific probe.

13. The method of claim 12, wherein the first label provides a chemiluminescent signal and the second label provides a fluorescent signal.

14. The method of claim 12, wherein the first label provides a fluorescent signal and the second label provides a chemiluminescent signal.

15. A method for determining the relative amount of two different experimental target nucleic acid sequences in a sample, comprising:

providing a nucleic acid array, wherein the array comprises a first feature that comprises first experimental probes that are complementary to a first experimental target sequence, and a second feature that comprises second experimental probes that are complementary to a second experimental target sequence;

contacting the array with:
(1) a sample that includes experimental target sequences that are labeled with a first label; and
(2) synthetic control target sequences that are labeled with a second label and that hybridize to the experimental probes on each of the first and second features, wherein the synthetic control target sequences compete with the experimental target sequences for binding of the experimental probes;

determining the intensity of any signal from the first and second labels in the first and second features;

determining the ratio of the intensity of the signal from the first label to the intensity of the signal from the second label for each of the first and second features; and comparing the ratios of the intensity of the signal for the first and second features to calculate the relative amount of first and second experimental target sequences in the sample.

16. A method for detecting the presence or absence or amount of an experimental target-specific probe on a substrate comprising:

exposing a substrate containing a first feature comprising an experimental target-specific probe and a control-specific probe to a labeled control target and a labeled experimental target, such that the labeled control target binds specifically to control-specific probe bound to the substrate, wherein the control-specific probe is not bound to the substrate by hybridization;

wherein the labeled control target comprises a first label and the labeled experimental target comprises a second label;

wherein the first label is distinguishable from the second label;

measuring a signal from labeled control target bound to control-specific probe to determine the presence or absence or amount of experimental target-specific probe; and wherein the first label provides a chemiluminescent signal and the second label provides a fluorescent signal.

17. A method for detecting the presence or absence or amount of an experimental target-specific probe on a substrate comprising:

exposing a substrate containing a first feature comprising an experimental target-specific probe and a control-specific probe to a labeled control target and a labeled experimental target, such that the labeled control target binds specifically to control-specific probe bound to the substrate, wherein the control-specific probe is not bound to the substrate by hybridization;

wherein the labeled control target comprises a first label and the labeled experimental target comprises a second label;

wherein the first label is distinguishable from the second label;

measuring a signal from labeled control target bound to control-specific probe to determine the presence or absence or amount of experimental target-specific probe; and wherein the first label provides a fluorescent signal and the second label provides a chemiluminescent signal.

* * * * *